(12) United States Patent
Jensen

(10) Patent No.: US 11,213,195 B2
(45) Date of Patent: Jan. 4, 2022

(54) DEVICE FOR USE IN HYSTEROSCOPY

(71) Applicant: LINA MEDICAL INTERNATIONAL OPERATIONS AG, Root (CH)

(72) Inventor: Jacob Kollerup Jensen, Hellerup (DK)

(73) Assignee: LINA MEDICAL INTERNATIONAL OPERATIONS AG, Root (CH)

( * ) Notice: Subject to any disclaimer, the term of this patent is extended or adjusted under 35 U.S.C. 154(b) by 200 days.

(21) Appl. No.: 16/348,831

(22) PCT Filed: Nov. 9, 2017

(86) PCT No.: PCT/EP2017/078753
§ 371 (c)(1),
(2) Date: May 9, 2019

(87) PCT Pub. No.: WO2018/087226
PCT Pub. Date: May 17, 2018

(65) Prior Publication Data
US 2019/0261845 A1 Aug. 29, 2019

(30) Foreign Application Priority Data

Nov. 9, 2016 (DK) .......................... PA 2016 70885

(51) Int. Cl.
*A61B 1/303* (2006.01)
*A61B 1/00* (2006.01)
(Continued)

(52) U.S. Cl.
CPC .......... *A61B 1/303* (2013.01); *A61B 1/00052* (2013.01); *A61B 1/0052* (2013.01); *A61B 1/0055* (2013.01); *A61B 1/0057* (2013.01); *A61B 1/00078* (2013.01); *A61B 1/015* (2013.01); *A61B 1/018* (2013.01); *A61B 1/045* (2013.01); *A61B 1/051* (2013.01);
(Continued)

(58) Field of Classification Search
CPC ......... A61B 1/303; A61B 1/307; A61B 17/42; A61B 17/4241
USPC ........................................................ 600/135
See application file for complete search history.

(56) References Cited

U.S. PATENT DOCUMENTS

| 4,719,924 A | 1/1988 | Crittenden et al. |
| 7,056,314 B1 | 6/2006 | Florio et al. |

(Continued)

FOREIGN PATENT DOCUMENTS

| CN | 1649537 A | 8/2005 |
| CN | 101099659 A | 1/2008 |

(Continued)

*Primary Examiner* — John P Leubecker
*Assistant Examiner* — Minqiao Huang
(74) *Attorney, Agent, or Firm* — Muncy, Geissler, Olds & Lowe, P.C.

(57) ABSTRACT

A device for visualization of internal tissue of a patient's uterus having a hand-held control unit, an elongated member, and an image capturing tip. To increase the manoeuvrability of the image capturing tip, the elongated member forms a straight portion extending along a straight axis and a curved portion forming a curvature away from the straight axis, the curved portion being between the image capturing tip and the straight portion. By rotation of an inner tube in an outer tube, the image capturing structure will move along a circular path without being rotated about the centre axis of the elongated member.

14 Claims, 7 Drawing Sheets

(51) Int. Cl.
*A61B 1/005* (2006.01)
*A61B 1/015* (2006.01)
*A61B 1/018* (2006.01)
*A61B 1/045* (2006.01)
*A61B 1/05* (2006.01)
*A61B 1/06* (2006.01)
*A61B 17/42* (2006.01)
*A61B 90/00* (2016.01)
*A61B 17/29* (2006.01)
*A61B 17/00* (2006.01)
*A61M 25/00* (2006.01)
*A61B 90/30* (2016.01)

(52) U.S. Cl.
CPC .......... *A61B 1/0684* (2013.01); *A61B 17/42* (2013.01); *A61B 17/4241* (2013.01); *A61B 90/37* (2016.02); *A61B 1/05* (2013.01); *A61B 17/29* (2013.01); *A61B 2017/00017* (2013.01); *A61B 2017/00115* (2013.01); *A61B 2017/00221* (2013.01); *A61B 2017/00309* (2013.01); *A61B 2017/00331* (2013.01); *A61B 2017/00734* (2013.01); *A61B 2017/00738* (2013.01); *A61B 2017/4216* (2013.01); *A61B 2090/064* (2016.02); *A61B 2090/309* (2016.02); *A61B 2217/005* (2013.01); *A61B 2217/007* (2013.01); *A61M 25/0054* (2013.01)

(56) References Cited

U.S. PATENT DOCUMENTS

| | | | |
|---|---|---|---|
| 2007/0135803 A1* | 6/2007 | Belson | A61B 1/00128 606/1 |
| 2007/0282304 A1 | 12/2007 | Ogura et al. | |
| 2008/0009676 A1 | 1/2008 | Wosnitza et al. | |
| 2008/0172033 A1 | 7/2008 | Keith et al. | |
| 2009/0192350 A1* | 7/2009 | Mejia | A61B 1/042 600/109 |
| 2009/0192355 A1* | 7/2009 | Mejia | A61B 1/0051 600/120 |
| 2011/0004157 A1* | 1/2011 | Dewaele | A61B 1/01 604/95.01 |
| 2011/0295066 A1* | 12/2011 | Fan | A61B 1/015 600/114 |
| 2012/0108902 A1 | 5/2012 | Frassica et al. | |
| 2013/0331651 A1 | 12/2013 | Iede | |
| 2014/0118515 A1* | 5/2014 | Lee | A61B 1/0055 348/65 |
| 2015/0282698 A1 | 10/2015 | Emanuel | |
| 2015/0366445 A1* | 12/2015 | Rutgers | A61B 1/267 600/120 |
| 2016/0015259 A1 | 1/2016 | Mody et al. | |
| 2016/0038014 A1 | 2/2016 | Molnar | |

FOREIGN PATENT DOCUMENTS

| | | |
|---|---|---|
| CN | 101897603 A | 12/2010 |
| CN | 102596064 A | 7/2012 |
| CN | 102697440 A | 10/2012 |
| CN | 102834066 A | 12/2012 |
| CN | 103040431 A | 4/2013 |
| CN | 103841880 A | 6/2014 |
| CN | 103889299 A | 6/2014 |
| CN | 104768604 A | 7/2015 |
| CN | 104936502 A | 9/2015 |
| CN | 105212887 A | 1/2016 |
| CN | 106137397 A | 11/2016 |
| CN | 106793918 A | 5/2017 |
| EP | 0554361 A1 | 8/1993 |
| EP | 2052672 A1 | 4/2009 |
| EP | 2596744 A2 | 5/2013 |
| JP | 2010213800 A | 9/2010 |
| JP | 4634520 B1 | 2/2011 |
| WO | WO-2011/060042 A1 | 5/2011 |
| WO | WO2012/060932 A2 | 5/2012 |
| WO | 12/151073 A2 | 11/2012 |
| WO | WO-2013/038720 A1 | 3/2013 |
| WO | WO-14039270 A1 | 3/2014 |
| WO | 2014065901 A1 | 5/2014 |
| WO | 14/115068 A1 | 7/2014 |
| WO | WO-14195491 A1 | 12/2014 |
| WO | 16/022759 A1 | 2/2016 |
| WO | WO2016/079141 A1 | 5/2016 |

\* cited by examiner

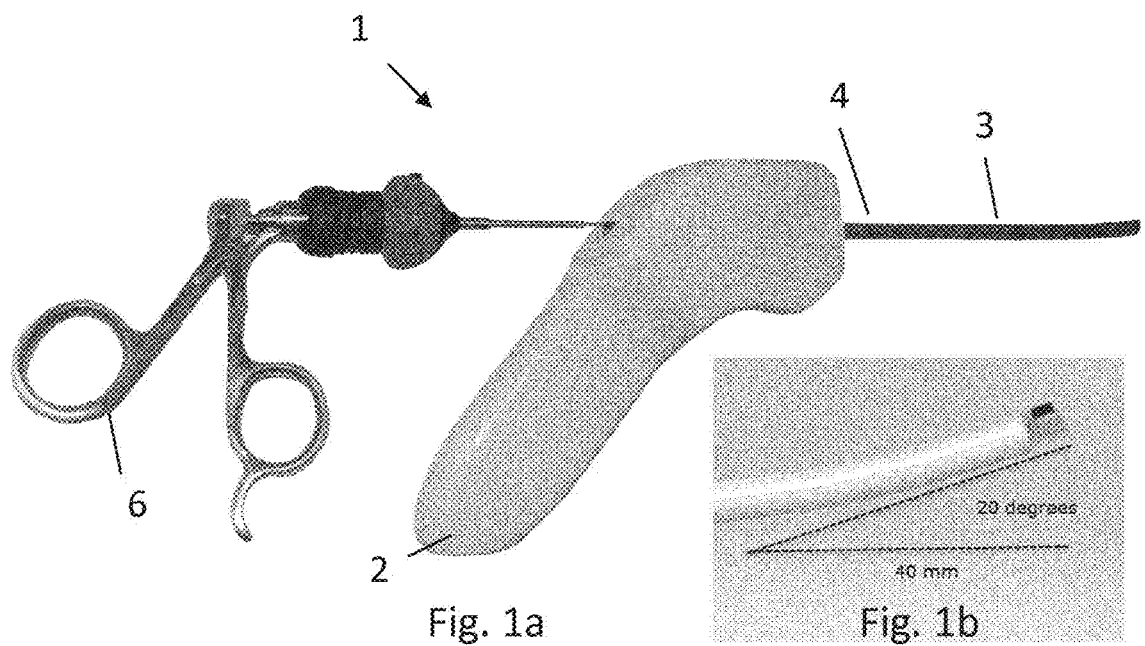
Fig. 1a  Fig. 1b
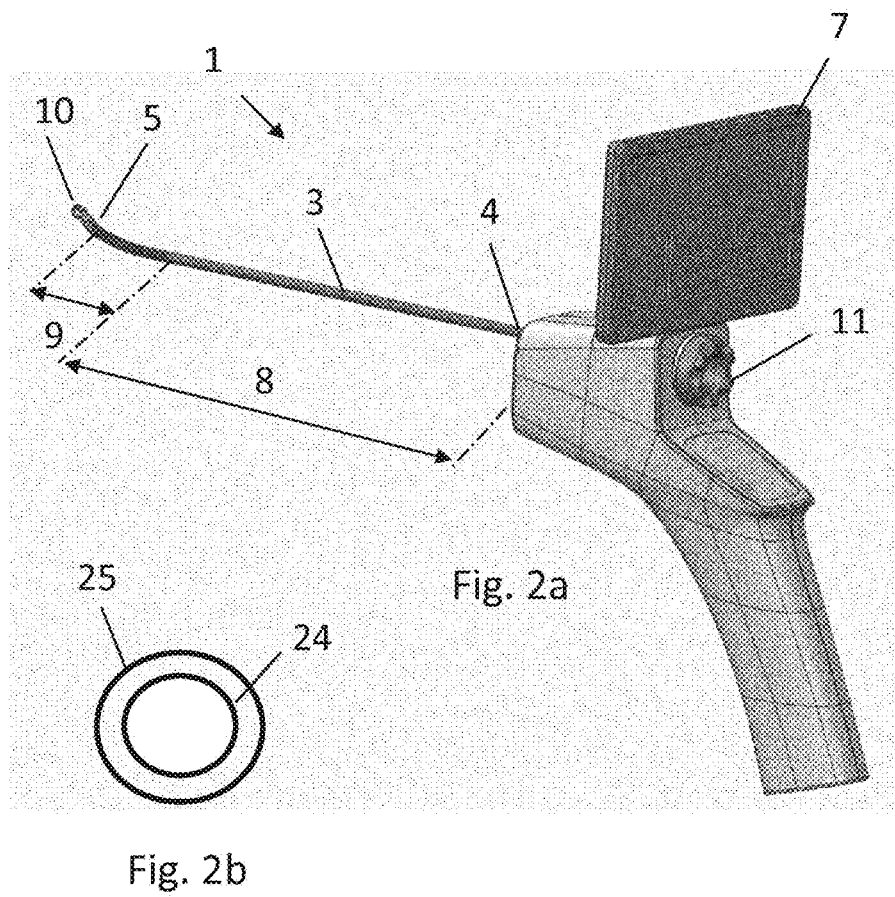
Fig. 2a
Fig. 2b

DEVICE FOR USE IN HYSTEROSCOPY

BACKGROUND OF THE INVENTION

Field of the Invention

The present invention relates to a portable device for use in hysteroscopy.

Brief Description of the Related Art

Gynaecologists use hysteroscopy in standard examination procedures, both office-based procedures and in hospital procedures where an endoscope is inserted into the uterus e.g. for inspecting the lining.

For the practitioner, the field of diagnostic imaging, for example hysteroscopy, has allowed for the viewing of objects, internal mechanisms and the like with minimal disruption.

Such imaging tools have been used in a wide variety of settings for detailed inspection, including but not limited to the use and application in the field of medicine.

In the medical field, the large amount of permanently or semi-permanently installed technical equipment is challenging. The costs for purchasing and costs for maintaining the equipment, and the complexity necessitate skills and training for the staff.

Additionally, the technical equipment takes up space, they require fixed power supply and/or supply of fluids etc., and they may be impossible to move close to the practitioner during the surgery and therefore they may sometimes be in the way for the staff and be difficult to use.

Sterility and re-usability are closely related. The fixtures of an operating room must typically be clean or even sterile before they can be used. Sterility can be accomplished by using a device only once, but typically, the large electrical fixtures including endoscopes and monitors of an operating room are too expensive to be used only once.

The existing endoscopes are typically two-unit devices composed of a relatively inexpensive scope with or without a camera. Typically, they include inexpensive single use fibre optic units configured for transferring the image to a more expensive control unit forming part of the fixture of an operating room.

The scope and control unit are connected by cables, e.g. including optical cables. The existing endoscopes are complicated to use and require adaption of settings between the scope and the control unit. Additionally, manoeuvrability of the scope inside narrow body cavities such as the uterus is complicated and the mechanical structure required for manoeuvring the scope is typically expensive an not suitable for single use devices.

SUMMARY OF THE INVENTION

It is an object of the invention to provide an improved device for hysteroscopy particularly relative to manoeuvrability and the ability to navigate inside the uterus.

Accordingly, the invention, in a first aspect, provides a device for visualization of internal tissue of a patient's uterus, the device comprising a hand-held control unit, an elongated member, and an image capturing tip. The control unit is dimensioned such that it can be held by a user's hand. The elongated member has a proximal end connected to the hand-held control unit and a distal end connected to the image capturing tip. The image capturing tip is configured to communicate video signals with a monitor.

The elongated member forms a straight portion extending along a straight axis and a curved portion forming a curvature away from the straight axis, the curved portion being between the image capturing tip and the straight portion.

The elongated comprises an inner tube and an outer tube, where the inner tube can rotate inside the outer tube. The inner tube has a rigid inner section which is located radially inside a flexible outer section of the outer tube—herein this is described as axially coextending positions of the inner section and outer section. The rigid inner section has a curved shape and by its rigidity, it deforms the flexible outer section. In that way, the rigid inner section forms the curvature of the curved portion of the elongated member by deflection of the flexible outer section.

By rotation of the inner tube in the outer tube is meant that the inner tube rotates relative to the outer tube. Due to the ability of the inner tube to rotate inside the outer tube, the outer tube will be deflected in different direction depending on the rotational orientation of the inner tube in the outer tube. Accordingly, a simple, reliable and efficient way of reorienting the image capturing tip inside the uterus is provided, and due to the separation of the inner tube from the cervix by the outer tube which extends about the inner tube, twisting of the lining in the cervix during the rotation can be avoided.

In one embodiment, the image capturing tip is fixed to the outer tube, and the outer tube is fixed to the hand-held control unit such that relative rotation between the image capturing tip, the outer tube and the hand-held control unit is prevented. According to this embodiment, the user may rotate the image capturing tip in the uterus by rotation of the hand-held control unit, and he may reposition the image capturing tip in the uterus without rotation of the image capturing tip by rotation of the inner tube in the outer tube. The rotation of the inner tube does not affect the rotational orientation of the image capturing tip, and that makes image processing easier and allows an non-rotated view even during repositioning by rotation of the inner tube in the outer tube.

At least the distal end of the elongated member and the image capturing tip are dimensioned for insertion into the patient's uterus through cervix. For that purpose, the cross section may particularly have a largest dimension of 5 mm. In one embodiment, the elongated member and/or the image capturing tip may have a circular shape with a diameter below 5 mm. such as 4 mm, or even below 4 mm. This is suitable for inspection of a human uterus through cervix.

By definition, the axial direction herein specifies the direction along the centre of the elongated member. Due to the curvature, this direction changes along the length of the elongated member.

Due to the curvature, the image capturing tip may be moved along a circular path about the straight axis. Movement may be effected simply by rotation of the elongated member. Accordingly, the user may obtain an easy way of reorienting the image capturing tip.

The control unit is dimensioned to be held by a user's hand and it may include various components such as a monitor. Accordingly, the surgeon may be able to manipulate and view internal organs by one device and without extensive cabling between separate devices.

The image capturing tip contains an image capturing structure configured for recording images and for communicating video signals with a monitor. The image capturing tip may e.g. comprise a CCD or any similar kind of electronic image capturing device.

Since the control unit is dimensioned to be held by a user's hand and since the elongated member is connected to or connectable to the control unit, the control unit may be used without connection to an external device. The device according to the invention therefore becomes easy to use directly upon removal from the package, e.g. without having to assemble cables or to attach an external camera or a monitor. This reduces the risk of errors, reduces the risk of combining non-compatible items, and reduces the risk of contaminating the device during handling.

The control unit may particularly be independently powered by a battery, and it may be fitted with different parts such as a monitor, a fluid flushing system, and other parts which are suitable for the procedure. In that way, the device may form a complete, independent, hysteroscopy device, e.g. suitable for single use.

The inner tube may comprise a straight inner section located in extension to the curved rigid inner section such that the rigid inner section is between the straight inner section and the image capturing tip. The straight inner section may be rigid or flexible, and it may be capable of transferring rotational movement to the curved rigid inner section.

In one embodiment, the inner tube extends between a control located at the hand-held control unit and the image capturing tip. The control may e.g. be in the form of a control knob which can be gripped by the user and used for rotating the inner tube. At the image capturing tip, the inner tube may be rotationally attached in a bearing structure enabling rotation of the inner tube without rotation of the image capturing tip. The straight inner section may particularly extend between the control and the rigid inner section, and the rigid inner section may extend between the straight inner section and the image capturing tip.

When the inner tube is rotated inside, and relative to the outer tube, the rigid inner section cyclically deforms the flexible outer section which thereby moves in a circular path. More particularly, the relative rotation may be effected e.g. in the following way:

a) the proximal end of the outer tube is fixed to the hand-held control unit such that rotation is prevented;

b) the image capturing tip is fixed to the distal end of the outer tube, more particularly such that the flexible outer section is close to the image capturing tip or directly connected to the image capturing tip. In that way, rotation of the image capturing tip may be prevented by the connection of the outer tube to the hand-held control unit;

c) the inner tube is rotationally fixed to the hand-held control unit such that it can rotate inside the outer tube. For this purpose, the inner tube is suspended on the hand-held control unit in a rotational suspension;

d) a control, e.g. in the form of the aforementioned control knob, is provided to allow the user to effect rotation of the inner tube in the outer tube. The control may include an electrical motor for turning the inner tube, or it may include a control for manually rotating the inner tube.

During use, the distal end of the elongated member and therefore also the image capturing tip is inserted through cervix into the uterus. Subsequently, the control is operated to cause rotation of the inner tube in the outer tube. By this rotation, the flexible section of the outer tube is deformed, and the image capturing tip is moved in a circular path without rotation about the centre axis of the elongated member. To effect rotation of the image capturing tip about the centre axis of the elongated member, the user may simply rotate the hand-held control unit which is fixed to the image capturing tip via the outer tube.

The flexible outer section may comprise a stiffening spring-element and a bendable sheath covering the spring-element. This combination provides flexibility to bend the outer tube in directions transverse to the axial direction but rigidity against radial collapsing of the outer tube. In one embodiment, the spring element is a helically coiled spring surrounded by a sheath e.g. of a heat shrinkable tube.

The image capturing tip may be constituted by a separate tip-element containing an image capturing structure e.g. in the form of a camera, e.g. a CCD and a camera lens. The separate tip-element may include a flow structure for release of fluid from the image capturing tip and for entering fluid into the elongated member via the image capturing tip. The image capturing tip may further include illumination means, e.g. including an LED.

The image capturing tip may be fixed to the outer tube e.g. via the above mentioned stiffening spring-element. In one embodiment, the image capturing tip forms a projection which engages a winding of a helically coiled spring.

The outer tube may be flexible throughout its length and it may thus adapt to the shape of the inner tube. In one embodiment, the outer tube comprises a stiff outer section in continuation of the flexible outer section such that it is only the flexible outer section which is shaped by the inner tube. The stiff outer section may particularly be between the flexible outer section and the hand-held control unit and it may form the straight portion of the elongated member. By the rigidity of the stiff outer section, the elongated member may become easier to insert through cervix.

The elongated member may form a tool conduit extending from an inlet at the hand-held control unit to a distal tool opening at or in the image capturing tip. The tool conduit may allow insertion of a surgical tool through the elongated member, e.g. a forceps. In one embodiment, the invention provides the combination of a device for visualisation and a forceps insertable through the tool conduit.

The device may form an outer conduit between the outer tube and the inner tube, and an inner conduit within the inner tube. The conduits may form a fluid flow path to and from the image capturing tip through the elongated member and thus allow extension of the uterus and flushing of the image capturing structure to provide improved visibility. In one embodiment, the inner conduit is constituted by the above-mentioned tool conduit—i.e. the inner conduit allows insertion of a surgical tool through the elongated member. The tool conduit may have a constant cross sectional size or it may have a cross sectional size which varies throughout the tool conduit.

The outer conduit may extend between an outer inlet and an outer outlet, and the inner conduit may extend between an inner inlet and an inner outlet. The inner conduit may be constituted by the tool conduit, and in that case, the inner outlet may be constituted by the distal tool opening.

The tool conduit and/or the inner conduit may have a constant cross sectional size or it may have a cross sectional size which varies throughout the tool conduit from the inner inlet to the inner outlet. In one embodiment, the cross sectional size is at most 3 mm such as at most 2 mm and it is smallest at the image capturing tip.

Particularly, the inner conduit may be configured for supplying fluid to the uterus via the image capturing tip and the outer conduit may be configured for discharging fluid out of the uterus. Accordingly, the inner inlet may be at or near the hand held control unit, and it may be configured for connection of the device to a fluid supply system. The inner outlet may be arranged in a distal end of the elongated member in the vicinity of the image capturing tip, it may be in a transition between the elongated member and the image capturing tip, or, the image capturing tip may form an extension conduit, and the inner conduit may be in fluid communication with the extension conduit in the image capturing tip such that the fluid can be released from the image capturing tip.

The outer inlet may be located in the distal end of the device, e.g. in the distal end of the elongated member, in the image capturing tip or in the transition between the image capturing tip and the elongated member such that fluid in the uterus can enter into the outer conduit. The outer outlet may be at, or near the handheld control unit, and it may be suitable for connection to the aforementioned fluid supply system or to a place of disposal for the fluid received from the uterus.

The device may comprise a fluid coupling allowing swiveling of the elongated member and thus the inner and outer tubes relative to a fixed connection structure by which the inner inlet and the outer outlet is connectable to the fluid flow structure and/or a place of disposal.

The coupling allowing swiveling may include a first space and a second space offset from each other in axial direction and separated from each other by a fluid separation barrier. The first space may form passage from an inlet to the inner conduit, and the second space may form passage from an outlet to the outer conduit. The spaces thereby facilitate connection of fluid supply and waste drainage to the inner conduit and to the outer conduit.

The coupling may be integrated in the hand held control unit to thereby allow connection of the fluid supply and waste drainage to the control unit.

The fluid separation barrier may form a bearing by which the outer and inner tubes may rotate relative to each other and such that a fixed distance is obtained between the outer and inner tubes.

The image capturing tip may, as mentioned, form a flow structure. Particularly, it may form an extension conduit from the inner outlet to a distal release opening. The extension conduit may additionally form the end portion of the tool conduit, and it may particularly form a portion which has a smaller cross sectional size than the remaining portion of the tool conduit, e.g. below 3 mm such as 2 mm or even below 2 mm. In one embodiment, the tool conduit, or at least that part formed by the extension conduit, has a circular cross section with a diameter of 2 mm.

The outer inlet may be between the image capturing tip and the curved portion of the elongated member. Particularly, the outer inlet may be in the transition between the image capturing tip and the elongated member. It may be constituted by one or more openings where the fluid can drain from the uterus into the outer conduit.

The inner tube may be rotationally suspended in the image capturing tip such that the inner tube and the outer tip is held concentrically by the image capturing tip. The image capturing tip may e.g. form a recess with a shape corresponding to the cross section of the inner tube such that the distal tip of the inner tube can be received in the image capturing tip. Particularly, the rotational suspension in the image capturing tip may form a liquid tight connection to the inner conduit to thereby prevent mixing of fluid in the inner and outer conduits.

The device may comprise a torsion element resisting rotation of the image capturing tip relative to the hand-held control unit. The torsion element may be constituted by an elongated element, e.g. a cable, a rod, or an elongated plate-shaped element extending between the image capturing tip and the hand-held control unit.

The torsion element may constitute an electrical connection between the image capturing tip and the control unit. In one embodiment, the torsion element is a PCB (printed circuit board) comprising electrical conductors for transfer of power and image signals from the image capturing tip to the hand-held control unit, and/or optionally for control signals and power to illumination means, valves or other features housed in the image capturing tip.

As mentioned previously, a control, e.g. in the form of a control knob, may be fixed to the inner tube and constitute the means for controlling rotation of the inner tube in the outer tube. The control may particularly extend in the axial direction rearwards out of the hand-held control unit. Particularly, the control may be integrated into the aforementioned coupling.

The image capturing tip may form an S-shaped portion forming an intermediate section extending transverse to opposite first and second ends, the first end forming an image capturing structure and the second end being fixed to the outer tube.

By means of the S-shape, the image capturing structure can be held offset from the centre axis of the elongated member. This may be useful, e.g. if it is desired to use surgical tools in combination with the device. Particularly, it may be useful for insertion of surgical tools through the aforementioned tool conduit.

The S-shaped portion enables surgical tools to be inserted through the tool conduit and to pass the image capturing tip. The tool opening which allows a surgical tool to exit the elongated member inside the uterus, could be placed between the second end and the intermediate section. In that way, the surgical tool may pass the first end and the image capturing structure.

Particularly, the distal tool opening of the tool conduit, and or the inner outlet may be in the S-shaped portion.

The S-shaped portion may have a bending characteristic different from that of the elongated member. Correspondingly, the first and second ends or the intermediate section of the S-shaped portion may have different bending characteristics.

The elongated member and/or the image capturing tip may be made from a material selected from the group consisting of: SEBS, PUR, and EVA.

The image capturing structure may be movable between a position where it partially hinders passage of a tool through the tool conduit and a position where the image capturing structure does not hinder the passing of the tool through the tool conduit.

In one embodiment the first end of the S-portion is more elastically deformable than the second end of the S-portion. This may make the distal end of the device more adaptable to the shape of cervix and the uterus, and it may reduce discomfort during insertion.

The elongated member may have a generally uniform cross-section throughout its length.

To reduce discomfort for the patient during introduction of the instrument through cervix it is an advantage if the instrument is small. Further, it is desired that the surface and geometry is generally smooth in order to make the instrument follow cervix smoothly during introduction. To reduce discomfort during the introduction of the elongated member e.g. through cervix, the outer diameter of the elongated member may be reduced towards the distal end, and it may terminate in a shape and size providing a largest cross section of 5 mm or even a largest dimension of 4 mm. This could e.g. be a circular cross section of 4 mm diameter.

The distal end of the elongated member may define a plane which is perpendicular to the center axis of the proximal portion of the elongated member, and the S-shaped portion may form a curved course between said plane and the proximal portion.

In a second aspect, the invention provides a method of operating a device according to the first aspect where rotation of the elongated member or at least an inner tube thereof is carried out to effect movement of the image capturing tip, particularly without rotation of the image capturing tip around the centre axis of the elongated member.

BRIEF DESCRIPTION OF THE DRAWINGS

In the following, embodiments of the invention will be described in further details with reference to the drawing in which:

FIGS. 1a and 1b illustrates an internal tissue visualization device according to the invention and a tool inserted in the tool conduit;

FIGS. 2a and 2b illustrate an internal tissue visualization device comprising a monitor mounted on the control unit according to the invention;

DETAILED DESCRIPTION OF THE PREFERRED EMBODIMENTS

Figure 3:
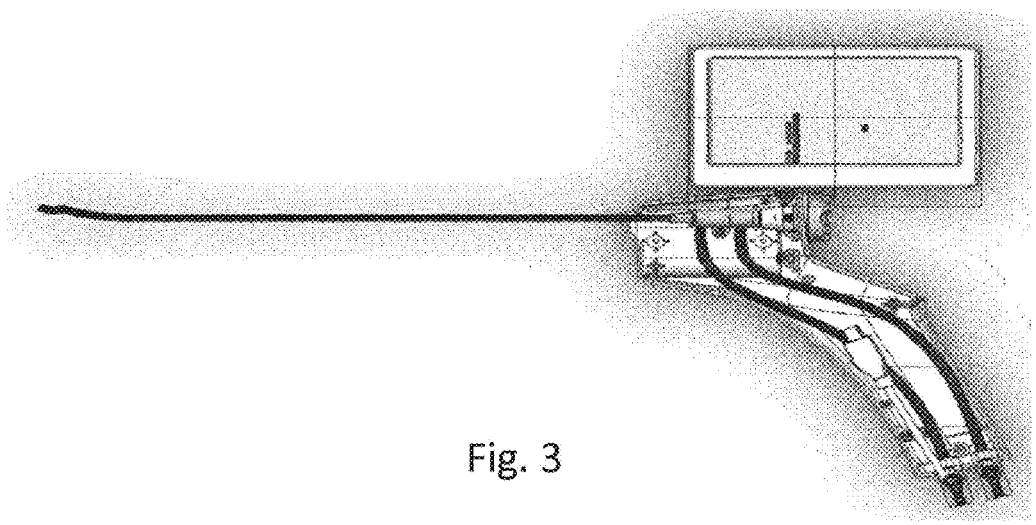
FIGS. 3-4 illustrate internal components of the hand-held control unit.

It should be understood that the detailed description and specific examples, while indicating embodiments of the invention, are given by way of illustration only, since various changes and modifications within the spirit and scope of the invention will become apparent to those skilled in the art from this detailed description.

Referring to FIGS. 1a, 1b, 2a, and 2b, the tissue visualization device 1 comprises an image capturing structure configured to capture pictures of tissue.

The device 1 comprises a hand held control unit 2 and an elongated member 3 connected to the control unit 2. The elongated member extends from a proximal end 4 to a distal end 5. The distal end is shown in FIG. 1b illustrating that the curved portion forms an angle of 20 degrees to the straight axis. The curved distal end is also only shown in FIG. 2a.

FIG. 1s illustrates a surgical tool 6 which is inserted in a tool conduit of the elongated member.

FIG. 2a illustrates a monitor 7 which can visualize the captured images. The monitor is attached to the hand held control unit to thereby enable use of the device completely independent on fixtures of an operating room.

FIG. 2a illustrates the entire elongated member including the straight portion 8 and the curved portion 9. The curved portion is between the image capturing tip 10 and the straight portion.

Generally, the elongated member 3 may be rigid and dimensionally stable such that it forms a good support for tools in the elongated tool conduit and such that it is insertable e.g. through cervix and such that the image capturing structure can be manipulated by manipulation of the control unit. The elongated member could e.g. be made of a rigid material such as metal or plastic. The elongated member 3 is relatively long and slim to reduce discomfort for the patient during insertion. The elongated tool conduit may be used for inserting tools such as a scissor, a forceps or a morcellator etc.

FIG. 2b illustrates a cross-section of the elongated member perpendicular to a center axis of the elongated member. In the herein disclosed embodiments, the elongated member has a circular cross section with an outer diameter of 4 mm. The elongated member forms an elongated tool conduit with a circular cross section and a having a smallest diameter of 2 mm.

The elongated member comprises an inner tube 24, and an outer tube 25. The inner tube is configured to rotate inside the outer tube and comprises a rigid inner section 69 (see FIG. 7) axially coextending a flexible outer section of the outer tube. The rigid inner section has a curvature and due to its rigidity, it deforms the flexible outer section and thereby forms the curvature of the curved portion 9 by deflection of the flexible outer section.

The control knob 11 is fixed to the inner tube and thereby enables a user to rotate the inner tube by rotation of the control knob.

The inner conduit within the inner tube allows fluid to be introduced into the uterus during surgery. Such fluids may typically be injected to expand the uterus during a medical procedure, or it may be injected to flush the image capturing structure and thereby create a clear sight. The fluid from the uterus is allowed to drain through the outer conduit between the inner tube and the outer tube. By this structure, fluid may constantly be circulated in the uterus and provide good visibility.

Figure 4:
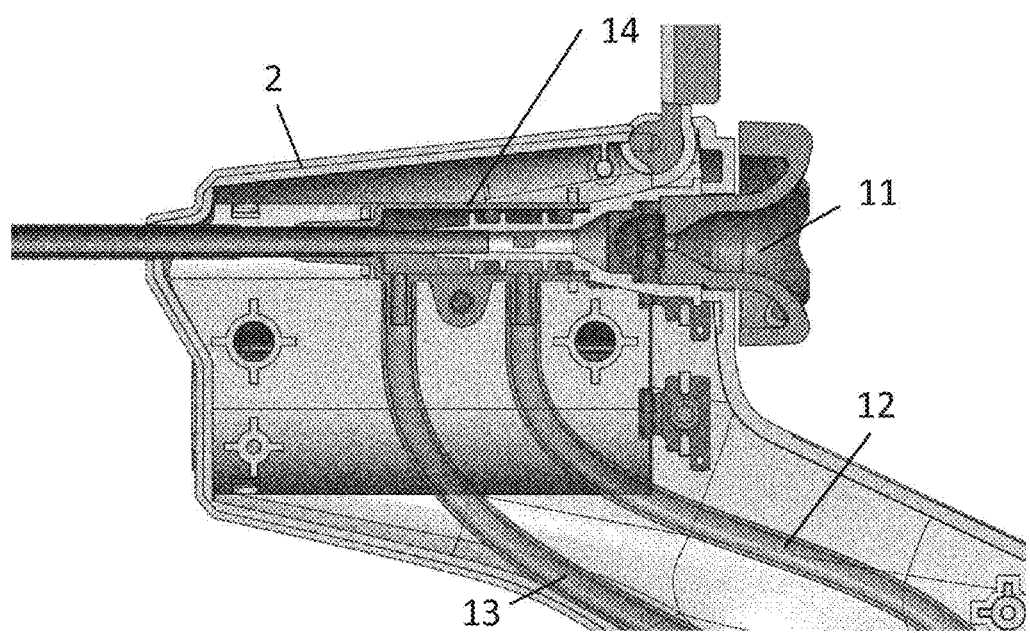

FIGS. 3 and 4 illustrate internal components of the device. The hand held control unit 2 houses a fluid system including an inlet 12 for entering fluid through the inner conduit into the uterus and an outlet 13 for draining fluid from the uterus through the outer conduit. The inlet 12 and outlet 13 are connected via the coupling 14.

Figure 5:
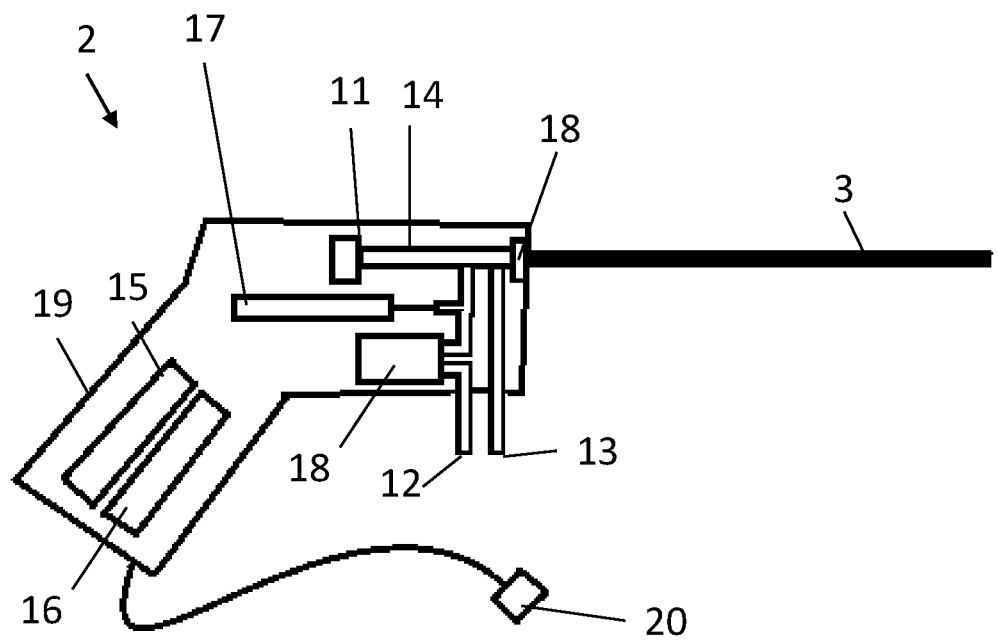
FIG. 5 illustrates schematically internal components of the device.

FIG. 5 schematically illustrates further elements housed in the control unit 2. Particularly, the control unit houses a battery 15, a controller 16 for processing data from the image capturing structure, and optionally communication means, e.g. comprising wireless transmission means, for transmitting the pictures to external systems. The control unit further houses a pressure sensor 17. The control unit may further comprise a flow control valve 18 for controlling the flow of liquid in the inner conduit. The liquid is used for flushing the image capturing structure and/or for extending the uterus.

The coupling 14 forms, in one end, the control knob 11, c.f. also FIG. 2. The coupling will be explained in further details later.

The control unit has the shape of a handle 19 adapted to fit in the hand of the user, further the control unit 2 comprises an interface 20 by which the device may communicate with external devices.

Figure 6:
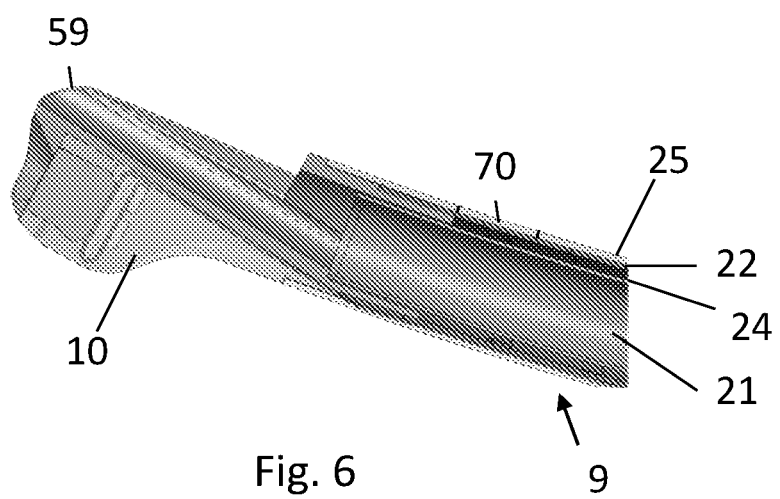
FIG. 6 illustrates a cross section of the image capturing tip.

FIG. 6 illustrates the curved portion 9 of the elongated member. In this view, the inner conduit 21 and the outer conduit 22 are clearly seen. The outer conduit 22 may extend between an outer inlet 70 and an outer outlet, and the inner conduit 21 may extend between an inner inlet and an inner outlet. The inner conduit may be constituted by the tool conduit, and in that case, the inner outlet may be constituted by the distal tool opening.

The image capturing tip 10 extends distally from the curved portion. The image capturing tip may have different shapes and will be explained in further details later. The inner tube 24 has a bended, curved shape and it is rigid at least concerning that part which is bended. The inner tube is, in the distal end, supported rotationally in a recess in the image capturing tip 10. The image capturing tip thereby forms a bearing for rotation of the inner tube relative to the image capturing tip.

The outer tube 25 comprises a two layer structure with an inner layer of a radially incompressible but yet bendable material such as spring, or a soft bendable, yet radially stiff material and an outer layer formed as a sheath of a soft pliable material, e.g. rubber. This is explained further with reference to FIG. 7.

Figure 7:
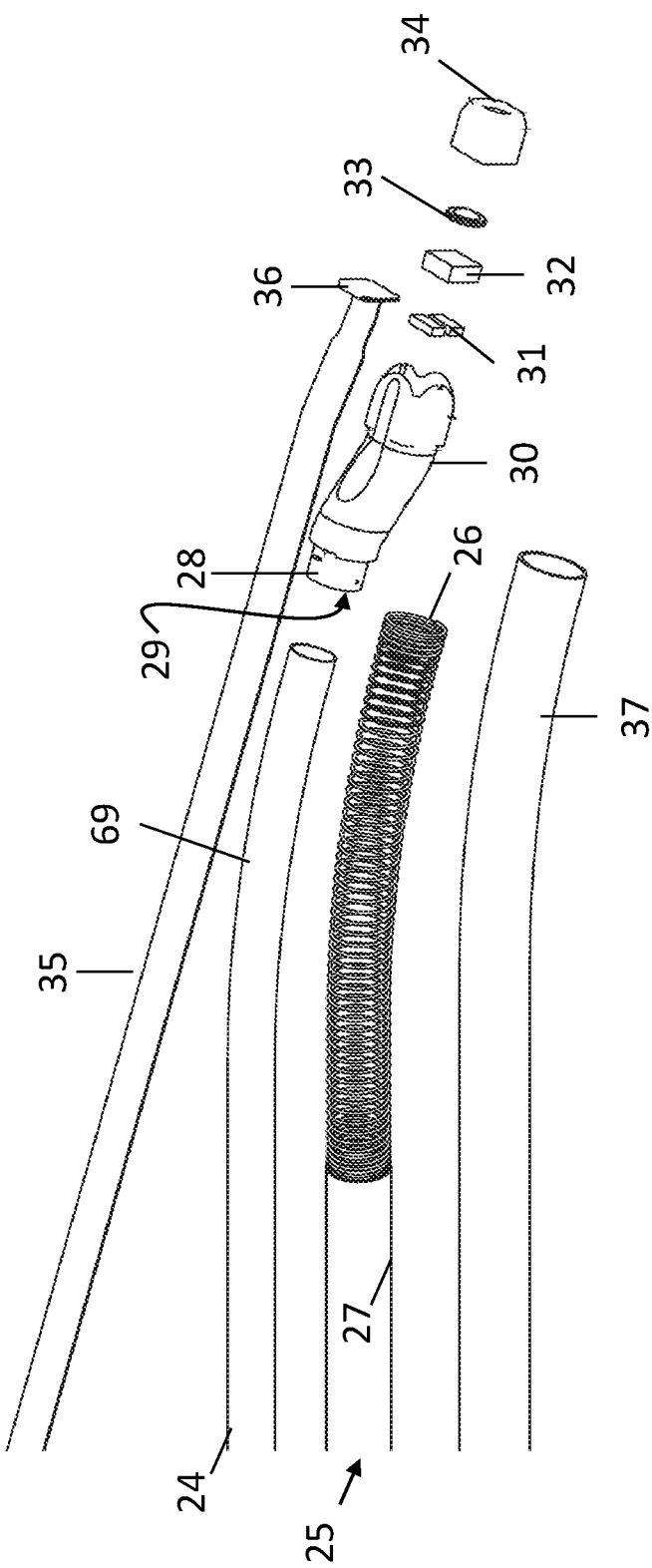
FIG. 7 illustrates an exploded view of the elongated member.

FIG. 7 illustrates the elongated member and the image capturing tip in a dis-assembled configuration. The elongated member comprises a rigid inner tube 24 with a curved shape. The inner tube is received in an outer tube. The outer tube has a two layered structure with an inner layer constituted by the tube 25. This inner layer tube comprises a flexible outer section 26 and a rigid outer section 27. The rigid outer section is made from steel and the flexible outer section is constituted by a helical spring or other bendable material with torsional rigidity allowing the inner tube to be rotated within the outer tube with out twisting the outer tube.

At the distal end of the elongated member, the flexible outer section of the outer tube is fixed to the flange 28 at the proximal end of the image capturing tip 10. The inner tube is received in a rotational bearing 29 formed inside the flange 28 in the proximal end of the image capturing tip 10.

The rotational bearing allows the inner tube to rotate concentrically within the outer tube. Since the image capturing tip is fixed to the outer tube, rotation of the inner tube will cause the body of the image capturing tip 10 to make a translatory movement along a circle, i.e. a movement where all points within the body are moving at the same velocity and in the same direction.

The image capturing tip may have different shapes. In FIG. 7, the image capturing tip has an S-shaped body 30 forming the mentioned attachment of the outer tube the flange 28 and the bearing 29 inside the flange.

An LED structure 31 with two LEDs, a glass layer 32 and a lens 33. A cap 34 holds the LED structure, the glass layer and the lens fixed to the S-shaped body 30.

The torsion element 35 extends between the image capturing tip and the hand-held control unit and forms in the distal end, a CCD 36. The torsion element forms a printed circuit board establishing electrical communication between the hand-held control unit and the CCD, and optionally also with the LED structure.

The outer tube has, as previously mentioned, a two layered structure with an inner layer constituted by the tube 25. This tube is covered in its entire length by the cover sheath tube 37. In an alternative embodiment, the cover sheath tube 37 covers only the flexible outer section. This is important, e.g. when the flexible outer section is water permeable, e.g. a helical spring. In this case, the cover sheath makes the outer tube water tight.

Figure 8A:
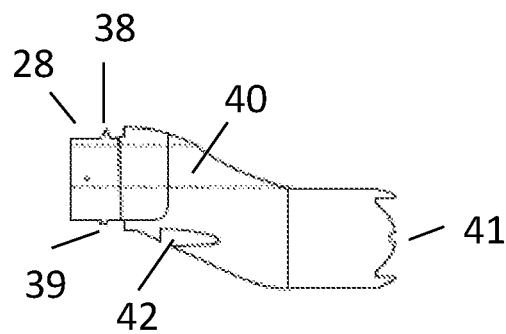
FIGS. 8A and 8B illustrate enlarged views of two different embodiments of a housing for the image capturing tip.
Figure 8B:
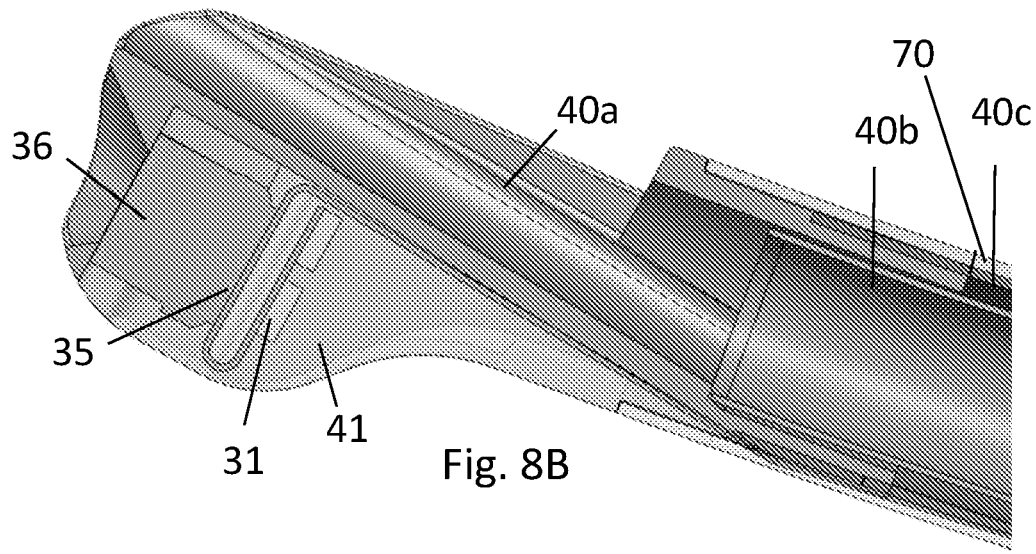

FIGS. 8A and 8B illustrate different embodiments of the image capturing tip.

In FIG. 8A, the image capturing tip has an S-shaped body. In this view, the flange 28 is shown with two projections 38, 39. The projections 38, 39 engage the windings of the helical spring which forms the flexible outer section 26 of the outer tube and thus fixes the outer tube to the image capturing tip.

The image capturing tip further comprises a tool conduit 40 forming an extension of a tool conduit through the elongated member. The tool conduit is indicated by the dotted lines in FIG. 8A and facilitates insertion of a tool through the elongated member and through half of the image capturing tip. The S-shape of the image capturing tip allows the tool to be inserted next to the camera and lens portion 41. The opening 42 allows the torsion element 35 to enter from the elongated member into the S-shaped tip portion where it can connect to electric devices, e.g. for signal transmission or for conducting electrical power to the LED etc.

In FIG. 8B, the image capturing tip extends along a straight line as an extension of the elongated member. Again, the image capturing tip forms a tool conduit 40a in extension to the tool conduit 40b in the elongated member. The camera and lens portion 41 is moulded in a transparent plastic material and houses the LED 31 and the CCD 36.

The CCD and LED are wired through the elongated member by the torsion element 35.

FIG. 8B illustrates that the tool conduit has a smaller cross sectional size at the image capturing tip than in the elongated member.

FIG. 8B further illustrates the outer conduit 40c.

Figure 9:
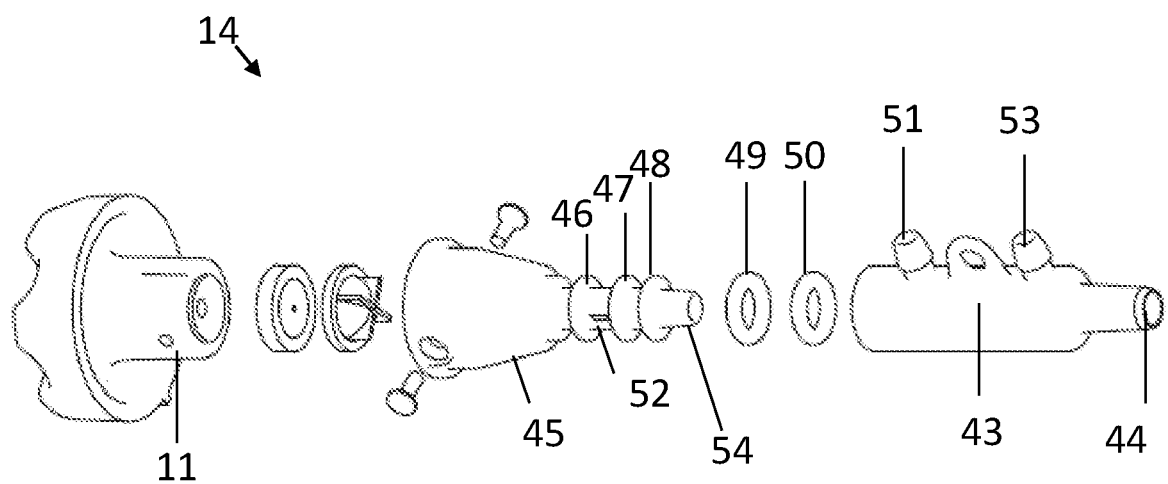
FIG. 9 illustrates an exploded view of the coupling.

FIG. 9 illustrates an exploded view of the coupling 14. The outer housing 43 forms a distal tip 44 shaped as a flange for receiving the outer tube thereon. The inner divider 45 forms three outward flanges 46, 47, 48 holding two sealing O-rings 49, 50. The O-rings establish a forward chamber and a rearward chamber. The forward chamber is located distal to the flange 48 and the rearward chamber is located between the flanges 46 and 47. The rearward chamber is in communication with the inner inlet 51 and forms an opening 52 into the inner conduit in the inner tube. The forward chamber is in communication with the outer outlet 53 and allows fluid drained from the uterus through the outer conduit between the inner and outer tube to be drained from the device.

The inner tube is fixed to the distal tip 54 of the divider 45 and the control knob 11 (comparable to the control knob 11 in FIG. 2) is fixed to the divider 45. By rotation of the control knob, the inner tube is rotated within the outer tube, and due to the curved shape of the inner tube, the image capturing tip is caused to move in a translator movement along a circular path.

Figure 10:
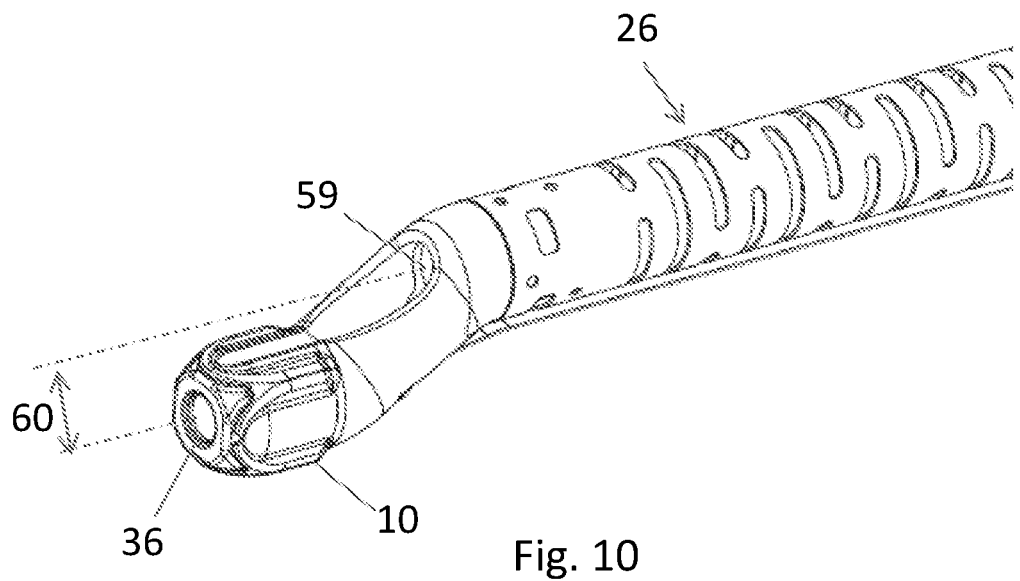
FIGS. 10 and 11 illustrate an S-shaped image capturing tip and an alternative embodiment of the flexible outer section of the outer tube.
Figure 11:
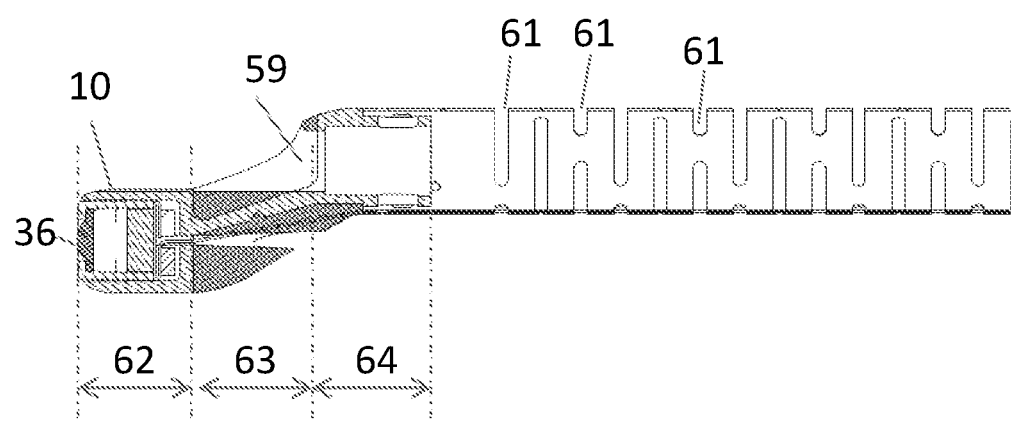

FIGS. 10 and 11 illustrate an S-shaped image capturing tip 10 and an alternative embodiment of the flexible outer section 26 of the outer tube. Due to the S-shape, the image capturing structure with lens and CCD 36 and the distal opening 59 of the tool conduit becomes off-set by the distance indicated by the arrow 60. A tool which is in the elongated conduit may therefore pass the image capturing structure unhindered.

The elongated member of this embodiment has an outer tube with a flexible outer section 26 where the flexibility is obtained by reducing the bending moment by the illustrated slots 61.

FIG. 11 illustrates three different sections 62, 63 64 illustrating the S-shape of the S-shaped image capturing tip. Whereas the forward and rearward sections 62, 64 are parallel, the intermediate section 63 is transverse to the other sections The Angle of the intermediate section 63 relative to the forward and rearward S-portions may particularly be less than plus or minus 70 degrees from perpendicular, such that the intermediate S-portion forms an angle between 20 and 170 degrees to the longitudinal direction of the elongated member.

Figure 12:
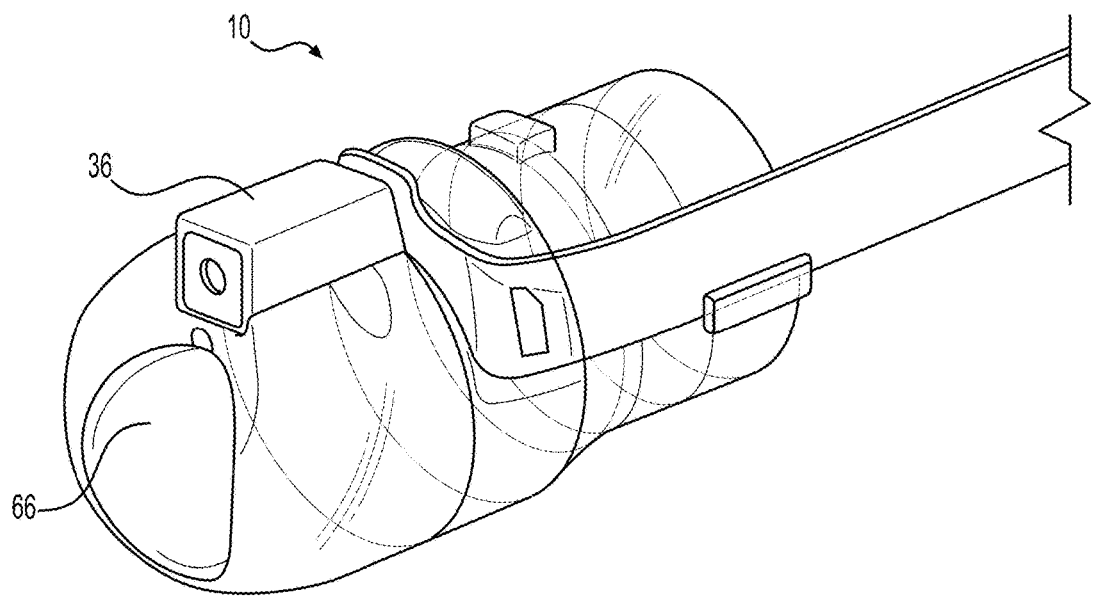
FIGS. 12-13 illustrate a straight image capturing tip.
Figure 13:
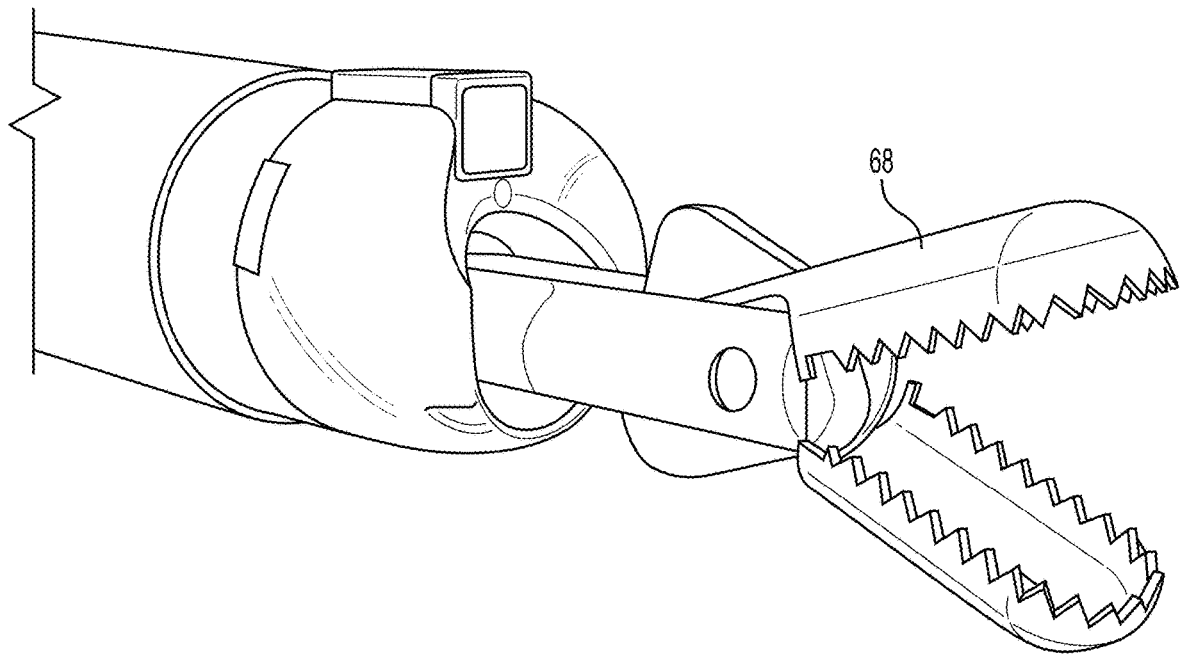

FIGS. 12 and 13 illustrate a straight image capturing tip 10 where the tool conduit 66 and the image capturing structure in the form of the CCD 36 are located within the dimension of the cross section of the elongated member. By this is meant that the image capturing tip can be projected onto a plane which is perpendicular to the distal end of the elongated member and thereby be within the dimension of the elongated member or at most have an area being 10 percent larger than the elongated member. Due to the straight shape, the image capturing tip is can be inserted more easily into the uterus through the relatively narrow cervix. The tool 68, in this case a forceps, which is in the elongated conduit may pass the image capturing structure unhindered due to the off-set between the image capturing structure and the tool conduit.

The invention claimed is:

1. A device for visualization of internal tissue of a patient's uterus, the device comprising
    a hand-held control unit being dimensioned to be held by a user's hand;
    an image capturing tip configured to communicate video signals with a monitor;
    an elongated member having a proximal end connected to the hand-held control unit and a distal end connected to the image capturing tip, the elongated member forming a straight portion extending along a straight axis and a curved portion forming a curvature away from the straight axis, the curved portion being between the image capturing tip and the straight portion, the elongated member comprising:
        an inner tube, the image capturing tip being fixed to an outer tube, the inner tube being rotationally suspended in the image capturing tip and suspended on the hand-held control unit in a rotational suspension; and
        the outer tube fixed to the hand-held control unit, the inner tube being rotational in the outer tube and comprising a rigid inner section extending inside a flexible outer section of the outer tube in an axial direction, the rigid inner section having a curvature which forms the curvature of the curved portion by deflection of the flexible outer section;
    an outer conduit between the outer tube and the inner tube; and
    an inner conduit within the inner tube, the outer conduit extending between an outer inlet and an outer outlet, and the inner conduit extending between an inner inlet and an inner outlet,
    wherein the rotational suspension of the inner tube in the image capturing tip forms a liquid tight connection to the inner conduit to thereby prevent mixing of fluid in the inner and outer conduits.

2. The device according to claim 1, wherein the flexible outer section comprises:
    a stiffening spring-element having radial stiffness but being bendable; and
    a bendable sheath covering the spring-element.

3. The device according to claim 2, wherein the image capturing tip is fixed to the outer tube via the stiffening spring-element.

4. The device according to claim 2, wherein the outer tube comprises a stiff outer section in continuation of the flexible outer section.

5. The device according to claim 4, further comprising a coupling element forming a first space and a second space between an outer housing and an inner divider, the outer tube being fixed to the outer housing, the inner tube being fixed to the inner divider, the first space being in fluid communication with the inner conduit, the second space being in fluid communication with the outer conduit, and the inner divider being rotationally received in outer housing.

6. The device according to claim 1, wherein the image capturing tip forms an extension conduit from the inner outlet to a distal release opening.

7. The device according to claim 1, wherein the outer inlet is between the image capturing tip and the curved portion.

8. The device according to claim 1, comprising a torsion element resisting rotation of the image capturing tip relative to the hand-held control unit.

9. The device according to claim 8, wherein the torsion element extends between the image capturing tip and the hand-held control unit.

10. The device according to claim 8, wherein the torsion element constitutes an electrical connection between the image capturing tip and the control unit.

11. The device according to claim 1, comprising a control knob fixed to the inner tube and being operable for rotating the inner tube in the outer tube.

12. The device according to claim 1, wherein the image capturing tip forms an S-shaped portion forming an intermediate section extending transverse to opposite first and second ends, the first end forming an image capturing structure and the second end being fixed to the outer tube.

13. The device according to claim 1, wherein the image capturing tip forms a straight shape being within a dimension of a cross section of the elongated member when projected onto a plane perpendicular to an axial direction of the elongated member.

14. The device according to claim 1, wherein the curved portion forms an angle of at least 15 degrees to the straight axis.

* * * * *